(12) United States Patent
Speiser et al.

(10) Patent No.: US 9,493,839 B2
(45) Date of Patent: Nov. 15, 2016

(54) NON-INVASIVE CANCER DIAGNOSIS (71) Applicant: Paul Speiser, Vienna (AT)

(72) Inventors: Paul Speiser, Vienna (AT); Robert Zeillinger, Blumau-Neurisshof (AT)

(73) Assignee: Paul Speiser, Vienna (AT)

( * ) Notice: Subject to any disclaimer, the term of this patent is extended or adjusted under 35 U.S.C. 154(b) by 0 days.

(21) Appl. No.: 14/027,105

(22) Filed: Sep. 13, 2013

(65) Prior Publication Data
US 2014/0011199 A1 Jan. 9, 2014

Related U.S. Application Data (63) Continuation-in-part of application No. PCT/EP2013/051899, filed on Jan. 31, 2013.

(30) Foreign Application Priority Data

Jan. 31, 2012 (EP) .................................. 12153340

(51) Int. Cl.
*C12Q 1/68* (2006.01)

(52) U.S. Cl.
CPC ........... *C12Q 1/6886* (2013.01); *C12Q 1/6806* (2013.01); *C12Q 2600/154* (2013.01); *C12Q 2600/156* (2013.01); *C12Q 2600/158* (2013.01)

(58) Field of Classification Search
CPC .............. C12Q 1/6806; C12Q 1/6886; C12Q 2600/154; C12Q 2600/156; C12Q 2600/158; C12Q 2600/112; C12Q 2600/118; C12Q 1/6883; C12Q 2600/178; C12Q 2600/106; C12Q 2600/136; C12Q 1/6809; C12Q 1/68
See application file for complete search history.

(56) References Cited

U.S. PATENT DOCUMENTS

| | | | |
|---|---|---|---|
| 6,607,894 B1 * | 8/2003 | Lopata et al. | 435/23 |
| 2002/0182619 A1 * | 12/2002 | Lillie et al. | 435/6 |
| 2003/0092019 A1 * | 5/2003 | Meyer et al. | 435/6 |
| 2003/0165831 A1 | 9/2003 | Lee | |
| 2011/0207756 A1 * | 8/2011 | Matsui | A61K 31/47 514/266.2 |
| 2012/0082978 A1 * | 4/2012 | Pilarski | C12Q 1/6841 435/6.11 |

FOREIGN PATENT DOCUMENTS

| | | |
|---|---|---|
| JP | 2000166557 | 6/2000 |
| WO | WO9924620 | 5/1999 |
| WO | WO/01/70979 | 9/2001 |
| WO | WO0175177 | 10/2001 |
| WO | WO2009006543 | 1/2009 |

OTHER PUBLICATIONS

Hegele (Arterioscler Throm Vasc Biol 2002 vol. 22 pp. 1058-1061).*
Lucentini (The Scientist 2004 vol. 18 pp. 1-3).*
Wu (Journal of Pathology 2001 vol. 195 pp. 53-65).*
Chan (G&P magazine 2006 vol. 6 No. 3 pp. 20-26).*
Duffy (European Journal of Cancer 2009 pp. 335-346).*
Bouquier (Familial Cancer 2001 vol. 10 pp. 655-657).*
Schildkraut (Cancer Res 2009 vol. 69 pp. 2349-2357).*
The GeneCard for TP53. Accessed Jul. 17, 2014 online at http://www.genecards.org/cgi-bin/carddisp.pl?gene=TP53&search=52a517e173e6fa70285ded085be0d86f.*
Buttitta (British Journal of Cancer 1997 vol. 75 No. 2 pp. 230-235).*
Debattista (Infect Dis Obstet Gynecol 2004 vol. 12 pp. 135-145).*
Karst (PNAS May 3, 2011 vol. 108 No. 18 pp. 7547-7552).*
Kuhn (Journal of Pathology 2012 vol. 226 pp. 421-426 pub online Dec. 23, 2011).*
Singer (Am J Surg Pathol vol. 29 No. 2 Feb. 2005 pp. 218-224).*
International Search Report, International Patent Application No. PCT/EP2013/051899, Apr. 11, 2013.
International Written Opinion, International Patent Application No. PCT/EP2013/051899, Apr. 11, 2013.
Altekruse S.F. et al. (eds), SEER Cancer Statistics Review, 1975-2007, National Cancer Institute. Bethesda, MD, http://seer.cancer.gov/archive/csr/1975_2007/, based on Nov. 2009 SEER data submission, posted to the SEER web site, 2010.
Bouquier, J et al., "Microsatellite instability analysis in uterine cavity washings as a screening tool for endometrial cancer in Lynch syndrome", Familial Cancer, 2011, vol. 10, No. 4, pp. 655-657.
Chen, Ken et al., "BreakDancer", Nat Methods, 2009, 6(9):677-681.
Cho, Kathleen, Arch Pathol Lab Med. 2009, 133(11):1775-1781.
de Kroon et al., BJOG: an International Journal of Obstetrics and Gynaecology, 2003, 110: 938-947.
DePristo, M.A. et al., Nature Genetics, 43: 491-498 (2011).
Dubeau L, Lancet Oncol, 2008, 9(12):1191-1197.
Gross, Amy L. et al., Journal of Oncology, 2010, Article ID 126295, doi: 10.1155/2010/126295.
Jemal, A et al., "Cancer Statistics," CA Cancer J Clin, 2009, 59:225-249.
Kuhn, E et al., J Pathol, 2012, 226(3):421-426.
Karishma, M et al., Frontiers in Biosciences E3, 2011, 625-634.
Pruthi, S et al., Mayo Clin. Proc., 2010, 85(12) 1111-1120.
Stirling J, Clin Oncol, 2005, 23(24):5588-5596.
Xie, C et al., BMC Bioinformatics, 2009, 10:80.

* cited by examiner

*Primary Examiner* — Amanda Haney
(74) *Attorney, Agent, or Firm* — Loza & Loza, LLP; Michael F. Fedrick (57) ABSTRACT

A non-invasive method for the diagnosis of adenocarcinoma or precursor lesions in a female subject and a kit for performing such diagnosis are provided. The method comprises the steps of (1) preparing epithelial cells of a sample of the subject obtained from a rinse of the uterine cavity and, optionally, the fallopian tubes, and (2) performing an analysis of the cells to determine an abnormality associated with ovarian or endometrial cancer, where the abnormality is indicative of adenocarcinoma or a precursor lesion.

9 Claims, 2 Drawing Sheets

SEQUENCE LISTING

<160> NUMBER OF SEQ ID NOS: 4

<210> SEQ ID NO 1
<211> LENGTH: 21
<212> TYPE: DNA
<213> ORGANISM: artificial sequence
<220> FEATURE:
<223> OTHER INFORMATION: Primer

<400> SEQUENCE: 1
tgtaacagtt cctgcatggg c                                    21

```
<210> SEQ ID NO 2
<211> LENGTH: 18
<212> TYPE: DNA
<213> ORGANISM: artificial sequence
<220> FEATURE:
<223> OTHER INFORMATION: Primer

<400> SEQUENCE: 2
acagcaggcc agtgtgca                                             18

<210> SEQ ID NO 3
<211> LENGTH: 15
<212> TYPE: DNA
<213> ORGANISM: artificial sequence
<220> FEATURE:
<223> OTHER INFORMATION: Probe

<400> SEQUENCE: 3
catgaaccag aggcc                                                15

<210> SEQ ID NO 4
<211> LENGTH: 15
<212> TYPE: DNA
<213> ORGANISM: artificial sequence
<220> FEATURE:
<223> OTHER INFORMATION: Probe

<400> SEQUENCE: 4
catgaaccgg aggcc                                                15
```

NON-INVASIVE CANCER DIAGNOSIS

CROSS-REFERENCE TO RELATED APPLICATIONS

This application claims the benefit of priority under 35 U.S.C. §120 from International Patent Application No. PCT/EP2013/051899, filed on Jan. 31, 2013 and entitled NON-INVASIVE CANCER DIAGNOSIS, which claims the benefit of priority under 35 U.S.C. §119 from EP Patent Application No. 12153340.0, filed Jan. 31, 2012. The disclosures of the foregoing applications are incorporated herein by reference in their entirety.

SEQUENCE LISTING

The entire content of a Sequence Listing titled "Sequence Listing.txt," created on Sep. 13, 2013 and having a size of 1 kilobyte, which has been submitted in electronic form in connection with the present application, is hereby incorporated by reference herein in its entirety.

FIELD OF THE INVENTION

The invention refers to a non-invasive method for the diagnosis of adenocarcinoma or their precursor lesions, in particular ovarian (OC) or endometrial cancer (EC), in a female subject by analyzing cells of the subject, a kit for the diagnosis of ovarian or endometrial cancer or their precursor lesions, and a screening method.

BACKGROUND

Epidemiology, Classification, Pathogenesis, Prognosis of OC and EC

OC is the leading cause of death from gynecologic malignancy in western civilized countries, with an estimated prevalence in Europe and the U.S. Pat. No. 1,752,600 in 2007 and 59,828 deaths yearly. Treatment and survival of the patients depend primarily on the stage of the disease. Of all OC patients only 25% are diagnosed at an early stage while the tumor is confined to the pelvis. In these cases the five-year survival rate is 80% to 90% and the disease can often be cured by the combination of surgery and chemotherapy and are increasingly frequently referred to as type I OC. Unfortunately, almost 75% of women affected have advanced stage disease with metastatic spread throughout the abdominal cavity or to retroperitoneal lymph nodes at the time of diagnosis; five-year survival rates fall to 19%-32% for advanced disease, despite maximum surgical effort and combination chemotherapy. This so called type II OC is the deadliest cancer in women, even more aggressive then lung cancer. (Altekruse S. F. et al., 2007, SEER Cancer Statistics Review, 1975-2007, National Cancer Institute. Bethesda, Md., based on November 2009 SEER data submission, posted on the SEER web site, 2010; GLOBOCAN 2008, International Agency for Research on Cancer, posted on to the Globocan website; Goff B. et al. (2010).

Pathologists currently employ a morphology-based classification systems to divide OC and EC into major subgroups based on degree of differentiation (tumor grade) and histologic subtype (e.g., serous, endometrioid, clear cell or mucinous).

Cho (Arch Pathol Lab Med. 2009; 133(11):1775-81) describes a new model for classifying ovarian tumors, in which the surface epithelial tumors is divided into two broad categories designated type I and type II tumors based on their pattern of tumor progression and molecular genetic changes. Type I tumors include low-grade serous carcinoma, low-grade endometrioid carcinoma, and a subset of clear cell carcinomas and mucinous carcinoma which develop in a stepwise fashion from well-recognized precursors. The type II tumors are high-grade and almost always have spread beyond the ovaries at presentation. Type II carcinomas include high-grade serous carcinoma, high-grade endometrioid carcinoma, undifferentiated carcinoma, probably some clear cell carcinomas and mucinous carcinomas, and malignant mixed mesodermal tumor (carcinosarcoma). Type II carcinomas presumably evolve rapidly, disseminate early in their clinical course, don't progress in a step-wise fashion (stage I to IV) and are highly aggressive. In contrast to type I tumors, type II tumors were thought of not having morphologically recognizable precursor lesions, before they were found in the fallopian tubes.

Gross et al. (Journal of Oncology 2010, Article ID 126295, doi: 10.1155/2010/126295) describe a study to identify precursor lesions of OC and EC and support the notion of an origin for serous OC in the fallopian tube. The precursor lesion of OC in the fallopian tube is called serous tubal intraepithelial carcinoma (STIC). Gross et al. also found very similar precursor lesions in the endometrium and, in analogy to the fallopian tube describe them as serous endometrial intraepithelial carcinoma (SEIC).

Dubeau (Lancet Oncol. 2008, 9(12):1191-7) argue that a large proportion of ovarian epithelial tumors, fallopian tube carcinomas and peritoneal carcinomas are of the same nature and could be regarded as single disease entity.

EC—carcinoma of the lining of the uterus—is the most common gynecologic malignancy in western civilized countries; in the USA approximately 42,160 cases are diagnosed annually and 7780 deaths occur. Fortunately, most cases are diagnosed at an early stage when surgery alone may be adequate for cure. Five-year survival rates for localized, regional, and metastatic disease are 96, 66, and 24 percent, respectively (Jemal A. et al. Cancer statistics, 2009. CA Cancer J Clin 2009; 59:225).

Type I EC is estrogen-dependent and associated with conditions that elevate estrogen levels. The precursor lesion, atypical endometrial hyperplasia, is well described. It is of endometrioid histology, well differentiated in most cases, is usually diagnosed at early stage because of irregular bleeding and therefore has a good prognosis. Type II of EC is not estrogen-dependent and of high grade endometrioid or serous or clear cell histology. In contrast to type I cancers, the vast majority especially of serous cancers are high grade, affect postmenopausal women, have no early symptoms, are diagnosed at advanced stage, behave more like OC and have a very poor prognosis.

Clinical Presentation and Diagnostic Workup of Suspected OC and EC

Unfortunately, most patients with epithelial OC or EC, in particular the serous carcinomas or type II carcinomas, experience few or no symptoms until the disease has widely metastasized. The lack of early symptoms and the absence of a reliable screening test to detect the disease early, result in women being diagnosed after the disease has spread beyond the ovary or uterus and has a poor prognosis. For these reasons, there is a clear medical need for earlier diagnosis of high-grade serous type II EC and OC. Furthermore, detection of STICs and SEICs could even result in prevention of high-grade serous type II EC and OC.

Irregular bleeding as the main symptom of EC is conventionally investigated by endometrial sampling and subsequent examination of the sampled tissue under the microscope. Endometrial biopsy can be performed as an office based procedure, when a speculum is inserted into the vagina, and a small flexible plastic tube is inserted through the cervix and into the uterus. A small amount of endometrium can be suctioned through the tube for histologic examination. Alternatively, a woman may undergo a more invasive procedure called "dilation and curettage" involving thorough sampling of the endometrium. This allows for diagnosis of early stage type I and usually endometrioid carcinoma. Bleeding from serous type II EC is examined the same way but the disease at the time of diagnosis is usually already advanced stage. Currently there is no method for early diagnosis of type II EC because of the lack of early symptoms.

Stirling (J Clin Oncol. 2005, 23(24):5588-5596) summarizes on the state-of-the-art diagnostic tests for OC. These include transvaginal ultrasonography and serum cancer antigen (CA-125) measurements. Transvaginal ultrasound involves the insertion of a probe into the vagina that uses ultrasound to create a picture. The specificity of both, ultrasound and serum CA-125 measurements, however is unacceptably low, and both tests are ineffective at detecting OC early enough to improve clinical outcomes. Definitive diagnosis of OC still relies on histological or cytological confirmation. These findings underline the importance for an effective test for early detection of OC.

WO01/75177A2 describes tumor markers in ovarian cancer and methods of diagnosing and prognosticating ovarian tumors employing samples, e.g. selected from the group consisting of a tissue biopsy, ovarian epithelial scrapings, peritoneal fluid, blood, urine, and serum.

WO99/24620A1 discloses primary screening for cervical dysplasia by measuring a biochemical marker of apoptosis and/or angiogenesis in each of a population of cells derived from convenient, superficial swabbing, sponging, scraping or lavage of superficial epithelial cells from the cervix.

US20030165831A1 describes methods for detecting ovarian cancers by determining a variety of markers. Malignant cells are detected in a patient sample, e.g. in an ovary-associated body fluid.

Genetic Changes in OC and EC

Detailed pathologic studies of prophylactically removed ovaries and fallopian tubes of asymptomatic women with germ-line BRCA 1 or BRCA2 (BRCA+) mutations have led to the discovery of an early malignant change in the fallopian tube referred to as STIC. STICS have linked many peritoneal and ovarian serous carcinomas to the fallopian tube. In over 90% of STICs and high-grade serous carcinomas but also in endometrioid OC and serous EC mutations in the TP53 tumor suppressor gene can be found. These mutations were demonstrated to represent clonal alterations, because the same mutations were found in STICSs of patients with advanced type II serous OC and SEICs in patients with serous EC (Karishma M. et al. 2011, Frontiers in Biosciences E3, January 1, 625-634, Kuhn et al. J. Pathol. 2011, doi: 10.1002/path.3023). Analysis of TP53 gene mutations and alterations in the p53 expression include sequence analysis and immunohistochemical staining. TP53 encodes a protein (p53) that acts as a central mediator of the cellular response to both genotoxic and non-genotoxic stress.

The PI3K/Akt pathway is another signaling pathway that is frequently altered in human cancers, including endometrial and ovarian endometrioid adenocarcinomas. This signaling pathway plays important roles in cell cycle progression, cell survival, response to nutrient availability, cell motility, and angiogenesis. Signaling via the PI3K pathway is initiated by interaction of specific ligands with plasma membrane-spanning receptor tyrosine kinases, such as EGFR (epidermal growth factor receptor), c-kit, and insulin-like growth factor receptor 1. The ligand/receptor interaction leads to the recruitment and activation of PI3K, which converts PIP2 (phosphatidylinositol-4,5 biphosphate) to PIP3 (phosphatidylinositol-3,4,5 triphosphate). PIP3 in turn transmits growth and survival signals by recruiting certain kinases such as the protein kinase B/Akt family of kinases and phosphoinositide-dependent kinase 1 (PDK1) to the membrane. In part through phosphorylation by PDK1, Akt is activated and phosphorylates specific downstream targets, many of which play key roles in the regulation of important cellular functions such as proliferation, cell size, apoptosis, response to nutrients and DNA damage. The lipid phosphatase Pten removes the D3 phosphate from PIP3, inactivating the signaling cascade and regenerating PIP2. In endometrioid adenocarcinomas, the PI3K/Akt pathway is often deregulated via inactivating mutations of PTEN or through activating mutations of PIK3CA, which encodes the catalytic subunit of PI3K. (see Cho (2009) Arch Pathol Lab Med. November; 133(11):1775-81).

Women with a germline BRCA1 or BRCA2 mutation are described to have a substantial risk of OC (Pruthi et al. Mayo Clin. Proc. 2010, 85(12) 1111-1120).

Saline Contrast Hysterosonography

The golden standard for the investigation of suspected benign endometrial pathology is transvaginal ultrasound. Differential diagnosis of abnormally thickened endometrium can be difficult since the endometrial linings of the anterior and posterior wall of the uterus touch each other. This circumstance makes it difficult to visualize benign endometrial tumors such as polyps. To separate the endometrial linings from each other a method called the saline contrast hysterosonography was developed. During this investigation a thin catheter is introduced into the uterine cavity through the uterine cervix and saline solution is instillated, separating the endometrial linings and allowing for better visualization. Saline contrast hysterosonography is a non-invasive, office based and very well tolerated investigation, and allows for routine application (de Kroon et al. 2003, BJOG: an International Journal of Obstetrics and Gynaecology 110, 938-947). During saline contrast hysterosonography approximately 10 mL normal saline are gently syringed into the uterine cavity and fallopian tube.

The preferred device to perform a rinse and/or lavage of the uterus and fallopian tubes is a catheter, e.g. a three way catheter. It may be inserted into the cervical canal and the balloon is inflated, e.g. with normal saline, to seal the cervical canal. If the cervical canal is too narrow to pass the catheter, it is optionally dilated, e.g. with Hegar dilators after application of Xylocaln spray.

According to a specific example, two 10 ml syringes—one of them containing 10 ml of normal saline—are connected to the two canals. With help of the gynecologic chair the patient is put into an upright position (anti Trendellenbur positioning). By pushing on the plunger of the normal saline containing syringe, the fluid is slowly syringed into the uterine cavity and tubes. Simultaneously the plunger of the empty syringe is gently pulled out, sucking the fluid from the uterine cavity and tubes. While one tube slowly empties, the other slowly fills up. After the lavage is finished a cap is put on the filled syringe and syringe is sent into the laboratory.

The development of an alternate and new test to detect OC or EC and their precursor lesions is imperative, in particular serous OC or EC or disease of early stages. Thus, it is the object to provide a technology that overcomes the current lack of a convenient, safe and cost-effective test possibly used for early diagnosis or in a screening program looking for cancer or precancerous lesions in women who have no symptoms of the disease.

SUMMARY OF THE INVENTION

The object is solved by the subject matter as claimed.

According to the invention there is provided a non-invasive method for the diagnosis of adenocarcinoma or their precursor lesions in a female subject by analyzing cells of the subject, in particular a genetic mutation, comprising preparing epithelial cells of a sample of the subject obtained from a rinse of the uterine cavity, and performing analysis of the cells to determine an abnormality associated with OC or EC, the abnormality being indicative of adenocarcinoma or their precursor lesions.

Preferably the analysis comprises molecular analysis, e.g. to determine cell or biomarker mutations. Specifically the abnormality is a genetic related abnormality, e.g. differential expression of one or more biomarkers of said cells.

Specifically said sample is obtained from the rinse of the fallopian tubes, for example the rinse of the uterine cavity and the fallopian tubes.

According to a specific embodiment, said sample is obtained by non-invasive rinse with normal saline solution (NISR), in particular such as used in saline contrast hysterosonography or sonohysterography. Upon rinsing, a sample may be withdrawn from the rinse or effluent for further analysis.

Specifically said cells may be separated from said sample and/or nucleic acid may be extracted, e.g. employing standard means and buffer.

A specific analysis method may employ an amplification-based method, such as employing PCR, or sequencing method, to determine a nucleic acid sequence, in particular to determine mutations in coding or non-coding regions.

The specifically determined abnormality is indicative of OC or EC, such as serous cancer or Type II carcinoma, or a precursor neoplasia thereof, such as intraepithelial carcinoma of the fallopian tubes and/or the endometrial lining, including serous intraepithelial carcinoma.

According to a specific embodiment, the method according to the invention is provided for the diagnosis of early stage OC and EC.

According to another specific embodiment, the method according to the invention is provided for the differential diagnosis of OC and EC in subjects with suspected OC or EC. The differential diagnosis is particularly understood as the determination of which of two or more diseases (herein OC and EC) with similar symptoms is the one from which the patient is suffering, by a systematic comparison and contrasting of the clinical findings.

The abnormality may be specifically determined by genotyping at least one mutation of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof.

In particular, the abnormality is determined by a gene expression profile employing qualitative and/or quantitative analysis.

The abnormality may specifically be determined by detecting loss of heterozygosity (LOH) or other chromosomal changes (e.g. copy number variations, CNVs) of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof, or of regions on chromosomes 1, 2, 3, 6, 7, 9, 12 and 20 (mostly gains) and chromosomes 4, 8, 11, 13, 14, 15, 17 and 22 (mostly losses). Structural rearrangements primarily involve deletions and unbalanced translocations involving 1p, 1q, 3p, 3q, 6q, 7p, 10q, 11p, 11q and 12q.

The abnormality may specifically be determined by detecting aberrant DNA methylation. Aberrant DNA methylation, specifically DNA hypermethylation, is the most common molecular lesion of the cancer cell, e.g. a change of DNA methylation in neoplasms is the silencing of tumor suppressor genes by CpG island promoter hypermethylation, which targets genes such as p16(INK4a), BRCA1, and hMLH1. Epigenetic events were also reported in a frequently deleted region on chromosome 8p22 that influence the expression of tumor suppressor candidate 3 (TUSC3), a putative tumor suppressor gene in ovarian cancer (Pits et al. Cancer. 2012 Oct. 23. doi: 10.1002/cncr.27850). The results indicated that TUSC3 expression is decreased significantly because of promoter methylation in malignant ovarian tumors compared with benign controls. Methylation status of the TUSC3 promoter had a significant and independent influence on progression-free and overall survival. Thus, the abnormality may specifically be determined by detecting TUSC3 hypermethylation.

Yet, the abnormality may specifically be determined by analysis at the cellular level by employing immunocytochemistry or fluorescence in situ hybridization (FISH).

According to a specific embodiment, the abnormality is determined by at least one of genotyping at least one mutation of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof, a gene expression profile employing qualitative and/or quantitative analysis, detecting loss of heterozygosity (LOH) or other chromosomal changes (e.g. copy number variations, CNVs) of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof, or of regions on chromosomes 1, 2, 3, 6, 7, 9, 12 and 20 (mostly gains) and chromosomes 4, 8, 11, 13, 14, 15, 17 and 22 (mostly losses). Structural rearrangements primarily involve deletions and unbalanced translocations involving 1p, 1q, 3p, 3q, 6q, 7p, 10q, 11p, 11 q and 12q, detecting aberrant DNA methylation, and analysis at the cellular level by employing immunocytochemistry or fluorescence in situ hybridization (FISH), in particular of any of the polypeptide expression products of the relevant genes, such as listed above.

According to a specific aspect of the invention, there is provided a kit for diagnosing adenocarcinoma in a female subject on the basis of an abnormality in a cell sample of said subject, such as used in a method according to the invention, which kit comprises an uterine catheter designed for non-invasive rinsing of the uterine cavity and collecting a sample of the rinse, means to prepare a fraction of epithelial cells of said sample, and reagents for analyzing said cells to determine an abnormality associated with OC or EC.

Specifically, said catheter is designed for use in NISR, in particular such as used in saline contrast hysterosonography or sonohysterography.

The kit may specifically comprise those reagents suitable for carrying out such analysis, preferably all necessary reagents provided in the kit form at the convenience of the operator, e.g. those essential reagents specifically used carrying out the analysis performed according to the invention, such as for genotyping at least one mutation of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof, a gene expression profile employing qualitative and/or quantitative analysis, detecting loss of heterozygosity (LOH) or other chromosomal changes (e.g. copy number variations, CNVs) of a biomarker selected from the group consisting of TP53, EGFR, PDGRFα, KIT, KRAS, BRAF, PIK3CA, PTEN, ARID1A, PPP2R1A, RB1, VHL, DICER, β-catenin (CTNNB1), CDKN2A, GATA4, RNASET2, BRCA1, BRCA2, BRIP1, PAX2, WT1, MYC, ERBB2, CSF1R, ECGF1, SRC, AKT2, RUNX3, FHIT, FGF3, CSMD3, FAT3, and MDM2, or combinations thereof, or of regions on chromosomes 1, 2, 3, 6, 7, 9, 12 and 20 (mostly gains) and chromosomes 4, 8, 11, 13, 14, 15, 17 and 22 (mostly losses). Structural rearrangements primarily involve deletions and unbalanced translocations involving 1p, 1 q, 3p, 3q, 6q, 7p, 10q, 11p, 11 q and 12q, detecting aberrant DNA methylation, and analysis at the cellular level by employing immunocytochemistry or fluorescence in situ hybridization (FISH), in particular of any of the polypeptide expression products of the relevant genes, such as listed above.

According to a specific aspect, the kit according to the invention may be used for screening a female population at risk of OC or EC, in particular including the screening for OC and/or EC.

According to a further aspect of the invention, there is provided a non-invasive method of preparing a sample for ex vivo diagnostic purposes by rinsing the uterine cavity and optionally the fallopian tubes of a subject with a physiologically accepted normal saline solution and retrieving a cell sample of the rinse.

DETAILED DESCRIPTION OF THE INVENTION

Specific terms as used throughout the specification have the following meaning.

As used herein, "abnormality" with respect to analyzing epithelial cells herein specifically refers to abnormality with respect to the nature and quantity of a biomarker, in particular its (nucleotide or amino acid) sequence and its expression, including the mutations, such as polymorphism in coding and non-coding sequences, or the level of gene expression. It further refers to an abnormality with respect to any of heterozygosity, chromosomal changes (e.g. amplifications, deletions, rearrangements) or cytochemistry.

As used herein, "biomarker" or "marker" refers to a molecule that indicates by its presence or (differential) expression, alone or in combination with other parameters, one or more aspects of an abnormality found in precancerous or cancer cells. The term particularly includes any polynucleotide having a mutation, e.g. a differential expression or any other alteration in expression level or activity that is associated with a disease or disorder. For example, the biomarker may be differentially expressed in precancerous or cancerous cells, at the transcription level or at the translation level. Thus, a biomarker may be any molecule that is a product of a nucleic acid molecule expression. Detection of a biomarker as indicating one or more aspects of an abnormality may be detection of its differential expression as compared to a reference or control.

Suitable biomarkers that may be analyzed for their expression to determine an abnormality according to the invention are of human origin and associated with adenocarcinoma, in particular with OC and/or EC, and are e.g. those listed in Table 1, including the UniGene accession numbers and gene symbols (HUGO nomenclature).

TABLE 1

List of biomarkers

| Name | Gene Symbol | Approved Name | HGNC ID | Location |
|---|---|---|---|---|
| AKT2 | AKT2 | v-akt murine thymoma viral oncogene homolog 2 | 392 | 19q13.1-q13.2 |
| ARID1A | ARID1A | AT rich interactive domain 1A (SWI-like) | 11110 | 1p36.1-p35 |
| BRAF | BRAF | v-raf murine sarcoma viral oncogene homolog B1 | 1097 | 7q34 |

TABLE 1-continued

List of biomarkers

| Name | Gene Symbol | Approved Name | HGNC ID | Location |
|---|---|---|---|---|
| BRCA1 | BRCA1 | breast cancer 1, early onset | 1100 | 17q21-q24 |
| CDKN2A | CDKN2A | cyclin-dependent kinase inhibitor 2A (melanoma, p16, inhibits CDK4) | 1787 | 9p21 |
| CSMD3 | CSMD3 | CUB and Sushi multiple domains 3 | 19291 | 8q23.3 |
| CSF1R | CSF1R | colony stimulating factor 1 receptor | 2433 | 5q32 |
| CTNNB1 | CTNNB1 | catenin (cadherin-associated protein), beta 1, 88 kDa | 2514 | 3p21 |
| DICER | DICER1 | dicer 1, ribonuclease type III | 17098 | 14q32.2 |
| ECGF1 | TYMP | thymidine phosphorylase | 3148 | 22q13 |
| EGFR | EGFR | epidermal growth factor receptor | 3236 | 7p12 |
| ERBB2 | ERBB2 | v-erb-b2 erythroblastic leukemia viral oncogene homolog 2, neuro/glioblastoma derived oncogene homolog (avian) | 3430 | 17q11.2-q12 |
| FAT3 | FAT3 | FAT atypical cadherin 3 | 23112 | 11q14.3 |
| FGF3 | FGF3 | fibroblast growth factor 3 | 3681 | 11q13 |
| GATA4 | GATA4 | GATA binding protein 4 | 4173 | 8p23.1-p22 |
| KIT | KIT | v-kit Hardy-Zuckerman 4 feline sarcoma viral oncogene homolog | 6342 | 4q11-q12 |
| KRAS | KRAS | v-Ki-ras2 Kirsten rat sarcoma viral oncogene homolog | 6407 | 12p12.1 |
| MDM2 | MDM2 | Mdm2 p53 binding protein homolog (mouse) | 6973 | 12q13-q14 |
| MYC | MYC | v-myc myelocytomatosis viral oncogene homolog (avian) | 7553 | 8q24 |
| PDGFRA or PDGRFα | PDGFRA | platelet-derived growth factor receptor, alpha polypeptide | 8803 | 4q12 |
| PIK3CA | PIK3CA | phosphoinositide-3-kinase, catalytic, alpha polypeptide | 8975 | 3q26.3 |
| PPP2R1A | PPP2R1A | protein phosphatase 2, regulatory subunit A, alpha | 9302 | 19q13 |
| PTEN | PTEN | phosphatase and tensin homolog | 9588 | 10q23 |
| RB1 | RB1 | retinoblastoma 1 | 9884 | 13q14.2 |
| RNASET2 | RNASET2 | ribonuclease T2 | 21686 | 6q27 |
| SRC | SRC | v-src sarcoma (Schmidt-Ruppin A-2) viral oncogene homolog (avian) | 11283 | 20q12-q13 |
| TP53 | TP53 | tumor protein p53 | 11998 | 17p13.1 |
| VHL | VHL | von Hippel-Lindau tumor suppressor | 12687 | 3p25.3 |
| BRIP1 | BRIP1 | BRCA1 interacting protein C-terminal helicase 1 | 20473 | 17q22.2 |
| BRCA2 | BRCA2 | breast cancer 2, early onset | 1101 | 13q12-q13 |
| PAX2 | PAX2 | paired box 2 | 8616 | 10q24.31 |
| WT1 | WT1 | Wilms tumor 1 | 12796 | 11p13 |
| RUNX3 | RUNX3 | runt-related transcription factor 3 | 10473 | 1p36 |
| FHIT | FHIT | fragile histidine triad gene | 3701 | 3p14.2 |

By "cancer" and "cancerous" is meant the physiological condition in mammals that is typically characterized by abnormal cell growth. Included in this definition are malignant cancers, as well as dormant tumors or micrometastases. Examples of cancer include OC and/or EC, which always include herein the serous adenocarcinoma, Type II disease or precursor lesions. Cancer is typically differentiated from benign neoplasm or tumors, e.g. by differential diagnosis.

By "control" or "control sample" is meant a biological sample representative or obtained from a healthy subject that has not been diagnosed with a cellular proliferative disorder. A control or control sample may have been previously established based on measurements from healthy subjects that have not been diagnosed with a cellular proliferative disorder. Further, a control sample can be defined by a specific age, sex, ethnicity, or other demographic parameters.

By "expression" is meant the detection of a product that is expressed or produced by a nucleic acid molecule by standard methods, which product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA. Typical diagnostic methods focusing on nucleic acids include amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Typical diagnostic methods focusing on proteins or polypeptides include binding techniques such as ELISA, immunohistochemistry, microarray and functional techniques such as enzymatic assays.

A "differential expression" is meant to be detected when determining an abnormality of the cells according to the invention, typically referring to a gene whose expression is activated to a higher or lower level in a subject suffering from a disease, specifically cancer, such as OC or EC, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, a differential gene expression is considered to determine an abnormality when there is at least an about two-fold, preferably at least about four-fold, more preferably at least about six-fold, most preferably at least about ten-fold difference between the expression of a given gene in normal and diseased subjects, or in various stages of disease development in a diseased subject. Furthermore, linear or non-linear models (like regression, neuronal networks, random forests) comprised of expression values of more than one gene indicative for the diseased status.

The terms "diagnostic" and "diagnosis" refer to identifying the presence or type of a pathologic condition and includes identifying subjects who are at risk of developing a specific disease or suffering from a disorder. Diagnostic methods differ in their sensitivity and specificity. While a particular diagnostic method may not provide a definitive diagnosis of a condition, it suffices if the method provides a positive indication that aids in diagnosis.

The terms "detection", "detecting", "determining", "analyzing", and the like are used interchangeably herein to refer to any form of measurement, and are herein specifically used in the context of determining abnormalities, such as biomarkers of cells and their differential expression indicating that the cells are either precancerous or cancerous.

As used herein the term "mutation" refers to alteration of the cell genotype or phenotype, e.g. altered biomarkers including alterations of the polynucleotides, their corresponding gene products and expression products, including nucleic acids and polypeptides or proteins, e.g. molecules with one or more point mutations or single-nucleotide polymorphism (SNP), fragments, variants, such as splice variants or isoforms.

As used herein the term "non-invasive" refers to methods that are non-surgical, e.g. not penetrating the body, as by incision or injection, or not invading tissue. In particular, the lavage of the internal uterus and optionally the tubal area is understood as a non-invasive technique of low strain, specifically used for sampling according to the present invention.

As used herein, "precancerous cells" or "precursor lesions" refer to cells of dysplasias and their precursory stages, as well as disseminated tumor cells.

By "reference" is meant a standard or control condition for comparison purposes. For example, a "reference sequence" is a defined sequence used as a basis for sequence comparison. A reference sequence may be a subset of or the entirety of a specified sequence, e.g. a segment of a full-length cDNA or gene sequence, or the complete cDNA or gene sequence The terms "subject", "patient" or "female" generally refer to a human, although the methods of the invention are not limited to humans, and may be useful in other mammals.

Therefore, the present invention provides a novel specific sampling technique and a method of diagnosing adenocarcinoma or its precursor lesions comprising such sampling technique. In particular, the invention provides diagnostic methods and kits useful for determining abnormalities in cells of the origin of adenocarcinoma or their precursor lesions, e.g. identifying a differential expression that identifies a subject as having or having a propensity to develop OC or EC. Such assays are specifically used to perform a molecular analysis or measure a mutation or an alteration in a nucleotide sequence, its activity or its expression level, including nucleotide sequence pattern and arrays, suitably provided in an ordered arrangement of array elements. Microarray-based platforms or high-throughput sequencing technologies may be specifically employed, e.g., SNP arrays.

The kit or devices according to embodiments of the present invention specifically includes means and in particular one or more devices for sampling and preparing a fraction of the sample including the epithelial cells, e.g. enriched in epithelial cells, eventually in the concentrated form.

In some embodiments, the kit according to the invention contains a device capable of both, rinsing the uterus cavity and sampling the rinse. In some other embodiments the kit according to the invention contains a combination of devices for such purposes. In further embodiments, the kit includes instructions for taking a sample from the subject, and using the kit for the diagnosis of the precancerous or cancerous disease.

Specifically samples are taken upon rinse of the uterine cavity in a suitable manner. A sample may comprise a specific amount of the rinse that is taken from the effluent or in situ when flushing the body cavity. Suitable amounts of the rinse sample are e.g. ranging from 0.5-20 mL, preferably 1-15 mL, more preferred 2-10 mL, such as about 5 mL (i.e. +/−1 mL). Means of obtaining rinse samples employ e.g. syringes or other containers known to those of skill in the art.

A fraction of the sample may be prepared which comprises epithelial cells, such as a separated cell fraction. Suitably a cell pellet may be produced upon centrifuging the sample, which provides for the concentration of cell density and separation of the medium. Suitable means are e.g., filtration, centrifugation—with or without one or more density gradient media—(flow assisted) magnetic-bead associated cell separation, non-magnetic cell separation (e.g. PluriSelect), cell microarray based cell manipulation (e.g. DEPArray, Silicon Biosystems), FACS, or equivalent technologies.

For example, microfluidic lab-on-a-chip devices provide unique opportunities for cell sorting and rare-cell detection. Microfluidic technology has been successfully used for microfluidic flow cytometry, continuous size-based separation and chromatographic separation.

The sample preparation may employ conventional buffer or other carriers, such as suitable to analyze the cells, in particular to perform molecular analysis of genetic information provided with the cells, or else to store genetic information for testing at a later time. Suitable carriers are, e.g., formalin, paraffin, RNAlater (QIAGEN), solutions with 2.5% to 15% DMSO.

In one embodiment, the kit includes reagents containing at least one agent that binds a biomarker, e.g. a polynucleotide or nucleic acid molecule whose sequence or expression is altered in OC or EC, specifically in the serous cancer or Type II cancer.

In specific embodiments, the kit comprises a sterile container which contains the binding agent.

Biomarkers useful for analyzing cells are typically those present in epithelial cells and indicative of OC or EC, in particular the serous carcinoma or Type II of the diseases, or any respective precursor lesion, such as those comprising precancerous cells.

Suitable biomarkers are known in the art, and include, but are not limited to, those listed in Table 1.

Additional biomarkers may be identified using methods known in the art. For example, biomarkers can be identified by looking at differential expression between normal and cancerous or precancerous cells at the mRNA level, by methods such as nucleic acid-based microarrays, high-throughput sequencing technologies, quantitative PCR based methods, and differential screening methods. Biomarkers can also be identified by looking at differential expression between normal and cancerous or precancerous cells at the protein level, by methods such as mass-spectrometry-based proteomics methods and protein chips or microarrays.

For diagnoses based on differential expression of the biomarkers and in particular relative levels of nucleic acids, a subject with an abnormality such as OC or EC disease will show an alteration, e.g. an increase of 10%, 20%, 30%, 40%, 50%, 60%, 70%, 80%, 90%, or more, in the amount of the molecules expressed or the presence or absence of a mutation, specifically including sequence mutation, variants or polymorphism, such as an SNP, compared to a control or reference.

In certain embodiments, a nucleic acid copy number is increased by at least two-fold fold. In some embodiments, a nucleic acid copy number is determined by hybridization-assays and/or amplification-based assays (e.g., fluorescence in situ hybridization (FISH), comparative genomic hybridization (CGH), or microarray-based CGH.

In some embodiments, the abnormality is determined by detecting an LOH of a biomarker or of a specific chromosomal region. The term "loss of heterozygosity" or "LOH", indicates that a region of a test genome has lost heterozygosity relative to a parent genome or to a diploid reference genome, which LOH may be indicative of proliferative disease.

For some embodiments, cells prepared or separated from the sample or cultured cells derived from the sample may be used for determining cellular abnormalities.

In some embodiments, cells isolated using the methods and devices of the present invention can be lysed, and one or more properties of the cells, or portions thereof, can be measured. Non-limiting examples of biological properties that can be measured in lysed cells include mRNA expression, protein expression, and DNA quantification. Additionally, in some embodiments, the cellular DNA can be sequenced, or certain sequence characteristics (e.g., polymorphisms and chromosomal abnormalities) can be identified using conventional techniques, e.g. FISH or PCR. In some embodiments of the present invention, information that can be obtained from the isolated cells includes identification or enumeration of particular genomic DNA, cDNA, or mRNA sequences.

In some embodiments, cells isolated using the methods and devices of the present invention are subjected to immunocytochemical analysis by flow cytometry or other analytical platforms.

In some specific embodiments, cellular tests may specifically employ visual determination of morphological abnormalities or some other embodiments typically used for detecting biomarkers, particularly polypeptides, e.g. in an immunoassay, an ELISA, immunocytochemistry, immunohistochemistry, flow cytometric analysis, radioimmunoassay, Western blot, etc.

Immunological methods are particularly suitable for detecting the expression of the markers according to the present invention. Therefore, binding agents, such as antibodies or antibody fragments, specific for each marker are used to detect expression. The markers can be detected by direct or indirect labeling of the binding agents, for example, with radioactive labels, fluorescent labels, hapten labels such as, biotin, or an enzyme such as horse radish peroxidase or alkaline phosphatase.

In some embodiments, the biomarker determined for the purpose of the invention is any known by the skilled person to be specifically expressed in cells at certain malignancy levels. For example, any subgroup of markers particularly relevant for OC/EC or precursor lesions may be determined.

In some embodiments, the method according to the invention comprises a multi-parameter analysis of cells in a sample, wherein these multiple parameters, preferably comprise at least TP53.

While individual markers are useful diagnostic markers, in some instances, a combination of markers provides greater predictive value than single markers alone. The detection of a plurality of markers in a sample can increase the percentage of true positive and true negative diagnoses and decrease the percentage of false positive or false negative diagnoses. Thus, preferred methods of the present invention comprise the measurement of more than one marker.

The analysis is specifically performed employing conventional techniques (e.g., temperature, pH, protein concentration, and ionic strength) known to the skilled artisan.

Typically, a sample is contacted with one or more probing agents that recognize biomarkers differentially expressed on precancerous or cancerous cells. The probing agents are labeled before or after they are brought into contact with the sample. The stained sample is then analyzed in a detection instrument, wherein measurements of the label, such as fluorescence intensities and light scattering are taken for cells examined. By analyzing one or more parameters, the condition of the examined cells can be assessed, e.g. when compared to a control or reference, and classified as normal or precancerous or cancerous, and the sample can be determined to be negative or positive for one or more cell abnormalities or adenocarcinoma, such as OC or EC.

For some applications, nucleic acid molecule probes are used to determine biomarkers in a sample. For example, the mRNA may be isolated from said sample according to standard methods, and cDNA may be produced and used as a template to make complementary RNA suitable for hybridization with a suitable probe by methods known in the art.

Probes may include nucleic acids, eventually hybridizing to the biomarker sequence to determine or exclude a specific mutation in said sequence. Hybridization and incubation conditions are usually adjusted such that hybridization occurs with precise complementary matches or with various degrees of less complementarity depending on the degree of stringency employed. Specifically bound probes may be detected, for example, using a label, such as for detecting fluorescence, or any other suitable detectable method known to the skilled person.

As an amplification-based method of molecular analysis, a PCR-based assay may be specifically employed. For example, a TaqMan-based assay may be used to quantify polynucleotides. Other suitable amplification methods include, but are not limited to, ligase chain reaction, transcription amplification, self-sustained sequence replication, dot PCR, and linker adapter PCR.

The invention specifically provides methods and kits for diagnosing and eventual monitoring OC or EC, e.g. for recurrence of a disease, the differential diagnosis in subjects suffering from a tumor, or the staging of disease, including early stage, but also later stage and metastatic disease.

The present invention specifically relates to methods and kits for screening subjects employing sampling by the non-invasive method according to the invention, e.g. by use of the kit according to the invention, to provide for information supporting the diagnosis of cancer. A population of subjects may be specifically screened that has an increased risk of developing proliferative disease.

Detection of amplification, overexpression, or overproduction of, for example, a biomarker gene or expression product can also be used to provide prognostic information or guide therapeutic treatment. Such prognostic or predictive assays can be used to determine early treatment of a subject prior to the onset of symptoms of cancer.

The diagnostic methods described herein can be used individually or in combination with any other diagnostic method described herein for a more accurate diagnosis of the presence of adenocarcinoma or their precursor lesions. Examples of additional methods for diagnosing such disorders include, e.g. examining a subject's health history, immunohistochemical staining of tissues, computed tomography (CT) scans, or culture growths.

The foregoing description will be more fully understood with reference to the following examples. Such examples are, however, merely representative of methods of practicing one or more embodiments of the present invention and should not be read as limiting the scope of invention.

Examples

1. Saline Hysterosonography and Sampling

Saline hysterosonography is performed according to de Kroon et al. (2003, BJOG: an International Journal of Obstetrics and Gynaecology 110, 938-947). During saline contrast hysterosonography 10 mL normal saline are gently syringed into the uterine cavity and fallopian tube. 5 mL is retrieved by sucking it back into the syringe and used as a sampling solution for further cell preparation and molecular analysis.

For non-invasive saline rinse (NISR) routine anesthesia or analgesia is not required. The insertion of the intrauterine catheter is often painless. A minority of women will experience some cramping sensations that can be prevented by subscribing a nonsteroidal anti-inflammatory drug such as mefenamic acid (500 mg) 30 minutes before the examination. After pregnancy is excluded, the patients need give consent for the procedure. Sterile conditions are secured and the patient is positioned in lithotomy position and a speculum is placed into the vagina.

After povidoneiodine solution or chlorhexidine gluconate is used to clean the cervical os, a 5 or 7 French sonohysterography catheter is inserted through the cervical canal. Before insertion the catheter needs to be flushed with normal saline to evacuate the air. After insertion the balloon in the tip of the catheter is inflated with 1-2 mL of saline to help hold it in place. Because the catheter is approximately 25 cm long, it will extend beyond the vaginal entrance even after the speculum is carefully removed, which is not invariably necessary. The speculum needs only to be removed if a saline hysterosonography is done in addition to NISR.

Occasional difficulties to insert the catheter can be overcome by changing the position of the speculum, by dilating the cervical canal or by the use of a guide wire. The use of a balloon catheter is not mandatory because adequate distention and rinse of the uterine cavity and fallopian tube can also be achieved with other type of catheters, though somewhat more difficult.

In circumstances where it is not possible to pass the catheter into the uterine cavity, a rinse is frequently still possible by placing the tip in the cervical canal as far up as possible and then inflating the balloon. If a saline hysterosonography should be performed in parallel to NISR the vaginal ultrasound probe is inserted. A 10 mL syringe filled with sterile saline is connected to the catheter. The amount of instilled fluid varies, depending upon patient comfort (cramps may occur) but 10 ml saline usually is not a problem. By pulling gently on the plunger the saline is suctioned back into the syringe, representing the rinse. Finally the balloon is collapsed and the catheter is pulled back or passively slips out of the uterus.

2. Lavage of the Uterine Cavity and Fallopian Tubes by the Means of the ALPINE Technique The ALPINE technique (Austrian Lavage Procedure for the Detection of tubal Intraepithelial Neoplasms) includes the following steps. First, a speculum is placed into the vagina and an antiseptic lotion is used for cleaning the cervix. Using a bullet forceps the cervix is grasped at 12.00 o'clock. A three way catheter is inserted into the cervical canal and the balloon is inflated with approximately 1 ml of normal saline to seal the cervical canal. If the cervical canal is too narrow to pass the catheter, it is dilated to 4 mm with Hegar's dilators. Because the catheter is approximately 25 cm long, it will extend beyond the vaginal entrance. Two 10 ml syringes, one of them containing 10 ml of normal saline are connected to the two tubes of the three-way catheter. The patient is put into anti-Trendellenburg positioning. By pushing on the plunger of the normal saline containing syringe, the fluid is slowly syringed into the uterine cavity and tubes. Simultaneously, the plunger of the empty syringe is gently pulled out, sucking the fluid from the uterine cavity and fallopian tubes. While one tube slowly empties, the other slowly fills up. After the lavage is finished, the balloon is deflated and the catheter is removed. A cap is put on the collection syringe and the syringe is sent to the laboratory.

3. Cell Preparation

Cells from the sampling solution are collected by filtration, centrifugation—with or without one or more density gradient media—(flow assisted) magnetic-bead associated cell separation, non-magnetic cell separation (e.g. PluriSelect), cell microarray based cell manipulation (e.g. DEPArray, Silicon Biosystems), FACS, or equivalent technologies. DNA, protein, and RNA molecules are prepared using known technologies, suitable for subsequent analyses technologies. For immunohistochemistry or FISH analyses cells can be fixed (e.g. with formalin) and embedded in adequate media like paraffin.

4. Molecular Analysis

Mutation analysis, CNV (copy number variation) analysis, SNV (single nucleotide variants) analysis, or whole transcriptome (expression) analysis are performed using high-throughput sequencing technologies. Brief, for DNA based analysis (mutation, CNV, SNV) DNA are used in total (whole genome DNA-seq) or pre-enriched for exons (exon-seq) or specific target genes or chromosomal regions (targeted DNA-seq, e.g. Fluidigms Access Array BRCA1, BRCA2 and TP53 Kit), DNAs sheared, and libraries prepared according to the used brand of the high-throughput sequencing technology and sequenced to an appropriate depth. After quality control, removing of adaptor sequences, PCR-duplicates and low-quality reads and eventually after trimming of three-prime low-quality bases, the reads are mapped to the genome (i.e. to the newest assembled human genome sequence, e.g. hg19 or GRCh37) using indel competent alignment programs like Stampy, Novoalign, or BWA. SNP/SNV calling and interpretation is performed with the Genome analysis toolkit (GATK) essentially following the publication of DePrisot et al. (Nature Genetics Volume: 43, Pages: 491-498: (2011)) and including local realignment around indels.

For CNV detection targeted (favored regions, see below) or exom enriched high throughput sequencing data are analyzed by BreakDancer (Nat Methods. 2009 September; 6(9):677-81. Epub 2009 Aug. 9.) and/or CNV-seq (BMC Bioinformatics. 2009 Mar. 6; 10:80.). The most prevalent numerical changes are gains of chromosomes 1, 2, 3, 6, 7, 9, 12 and 20 losses of chromosomes 4, 8, 11, 13, 14, 15, 17 and 22. Structural rearrangements primarily involve deletions and unbalanced translocations involving 1p, 1q, 3p, 3q, 6q, 7p, 10q, 11p, 11q and 12q.

Whole genome expression analysis is performed by RNA-seq of either poly A enriched (oligo-dT based enrichment) or rRNA depleted (RiboMinus (Invitrogen), Ribo-Zero (epicentre)) RNA. RNA or cDNA are sheared enzymatically, chemically, or physically (ultrasound, nebulization) and libraries produced according to the used brand of the high-throughput sequencing technology and sequenced to an appropriate depth. For multiplexing, indices are added to the adaptors. Reads are mapped with an RNA-seq compatible alignment program (e.g. RNA-Seq Unified Mapper (RUM), STAR, TopHat). After counting of aligned reads (cufflinks, HTseq-count) differential or absolute gene expression is determined (cufflinks, cuffdiff, DEGseq, DESeq, SAMseq, edgeR, NOISeq).

Using statistical methods for multivariable model building (lasso, elastic net, supervised PCA, neuronal networks, support-vector machines, random forests) discriminative expressed genes, mutations/SNPs, SNVs, CNV and chromosomal aberrations are determined and validated by gold standard methods (e.g. qPCR or digital PCR based, pyrosequencing).

5. Exemplary Process to Determine a Biomarker Indicative of OC and/or EC, or a Precursor Malignancy Thereof, in a Patient Sample Sampling The patient is positioned on the gynecologic chair. The ultrasound examination gives the information about the exact position of the uterus and the cervix. A gynecologic speculum is inserted into the vagina and the cervix is visualized. The cervix is cleaned with an antiseptic lotion. Using a pointed forceps the cervix is grasped at 12.00 o'clock position. A three way catheter is inserted into the cervical canal and the balloon is inflated with normal saline. The canal is now sealed. If the cervical canal is too narrow to pass the catheter, it is dilated with Hegar dilators after application of Xylocaln spray.

Two 10 ml syringes one of them containing 10 ml of normal saline are connected to the two canals. With help of the gynecologic chair the patient is put into an upright position (anti Trendellenbur positioning). By pushing on the plunger of the normal saline containing syringe, the fluid is slowly syringed into the uterine cavity and tubes. Simultaneously the plunger of the empty syringe is gently pulled out, sucking the fluid from the uterine cavity and tubes. While one tube slowly empties, the other slowly fills up. After the lavage is finished a cap is put on the filled syringe and syringe is sent into the laboratory. This technique is called the ALPINE technique (Austrian Lavage Procedure for the Detection of tubal Intraepithelial Neoplasms).

The aspirate is centrifuged for 10 minutes at 15000 rpm. Supernatant is removed and the remaining cell pellet frozen at −80° C.

Subsequently, DNA of the cell pellet re-suspended in 250 µl is isolated. For DNA isolation the QIAamp MinElute Media Kit (QIAgen) is used according to the manufacturer's protocol.

Determination of TP53 as Exemplary Tumor Marker

For detection of tumor cells the fact that already very early in the progression of ovarian cancer in most of the patients, a mutation of the TP53 gene is likely to occur is used. The mutation is detected for example through digital PCR, using the QX100™ Droplet Digital™ PCR System from Bio-RAD. The type of TP53 mutation present in the primary tumor tissue is verified in the DNA isolated from the lavage. Therefore, an assay targeting this specific TP53 mutation is designed. It uses a forward and a reversed primer, which bind upstream and downstream the targeted region. A PCR product of ~100 bp is produced. Probes which are specific for the particular TP53 mutation, respectively wild type are used. These probes must have a melting temperature Tm 5-10° C. higher than the primer Tm. The probes consist of a fluorophore covalently attached to the 5'-end, for the mutation specific probe FAM (6-carboxyfluorescein), for the wild type VIC and a quencher on the 3' end MGB (minor groove binder). The PCR components (Master mix, primers, probes, DNA) are mixed and 20 µl of this mix are used for droplet generation using the QX100™ Droplet Generator from Bio-RAD, according to manufacturer's protocol. By that the PCR Assay is partitioned into 20,000 water in oil droplets. The emulsion is then transferred to a 96-well PCR plate, heat sealed and PCR is performed. Annealing temperature is adapted to previous optimized temperature, depending on which kind of TP53 mutation is going to be detected. Through the QX100™ Droplet Reader (Bio-RAD) each droplet is counted as negative or positive for the specific target DNA and if a cell carrying a TP53 mutation was present in the lavage, a fluorescent signal is detected.

The TP53 gene expression, specifically the mutation and overexpression of p53, is indicative of a disease, specifically OC and/or EC, or a precursor malignancy thereof.

According to the Example, the Following P53 Mutation is Determined Employing the Primer and Probes Described Herein:

```
Mutation in codon 248 (g.14070G > A, p.Arg248Gln)
                                              (SEQ ID 1)
forward PCR primer: tgtaacagttcctgcatgggc (SEQ ID 2)
reverse PCR Primer: acagcaggccagtgtgca (SEQ ID 3)
probe 1: 5'-FAM-catgaaccagaggcc-MGB-3'

(SEQ ID 4)
probe 2: 5'-VIC-catgaaccggaggcc-MGB-3'
```

TP53 Gene: UniProtKB: P04637

This gene encodes tumor protein p53, which acts as a tumor suppressor in many tumor types; induces growth arrest or apoptosis depending on the physiological circumstances and cell type; and is involved in cell cycle regulation as a trans-activator that acts to negatively regulate cell division by controlling a set of genes required for this process. One of the activated genes is an inhibitor of cyclin-dependent kinases. Apoptosis induction seems to be mediated either by stimulation of BAX and FAS antigen expression, or by repression of Bcl-2 expression. Implicated in Notch signaling cross-over. Prevents CDK7 kinase activity when associated to CAK complex in response to DNA damage, thus stopping cell cycle progression. Isoform 2 enhances the transactivation activity of isoform 1 from some but not all TP53-inducible promoters. Isoform 4 suppresses transactivation activity and impairs growth suppression mediated by isoform 1. Isoform 7 inhibits isoform 1-mediated apoptosis.

Alternatively a method of targeted deep sequencing of genetic alterations may be used, e.g. those known to occur in ovarian and endometrial and tubal cancer frequently.

6. Determine a Biomarker Indicative of OC and/or EC, or a Precursor Malignancy thereof, in a Patient Sample For the proof of principle that tumor cells from HGSCs can be found in the lavages of the uterine cavity, uterine lavages were collected before a surgical intervention for suspected ovarian malignancy at our institution. If malignancy was proven on frozen section, tumor tissue was collected and DNA prepared for further analysis. TP53 mutations, characteristic for HGSC were determined in tumor tissues. DNA of cells obtained from lavage specimens was analyzed for the presence of cancer specific mutations using digital droplet PCR (ddPCR).

So far, several ddPCR systems have been established for specific TP53 mutations, identified in tumor tissues. In four of the corresponding lavage specimens, the respective mutations could be detected with a rate between 0.013% and 5.96%. The presence of cancer cells in the lavage fluid was further confirmed through p53 immunofluorescence staining. In addition, we detected TP53 mutated cells (23.80%) in the lavage fluid of a patient with metastasized signet ring carcinoma.

Two ovarian cancer patients with a KRAS mutation in the tumor tissue were also analyzed; KRAS-mutated cells were present in the corresponding lavage samples as well (0.25%, 0.37%). Preliminary results show that tumor cells can indeed be collected by the ALPINE technique in patients with HGSC or other malignant abdominal diseases.

Lots of cells and cell clusters get shed from the surface of STICs. These exfoliated cells from STICs get transported into the uterine cavity via the fallopian tubes. The ALPINE technique allow for collecting those cells originating from STICs. Those cells will be detected either by means of molecular techniques like next generation sequencing or other detection systems like immunocytochemistry. This will result into the first screening technique for HGSC, first in the high risk population like women with a germ line mutation in the BRCA 1 or 2 gene. Later the ALPINE technique will allow for a screening also in the general population.

Figure 1:
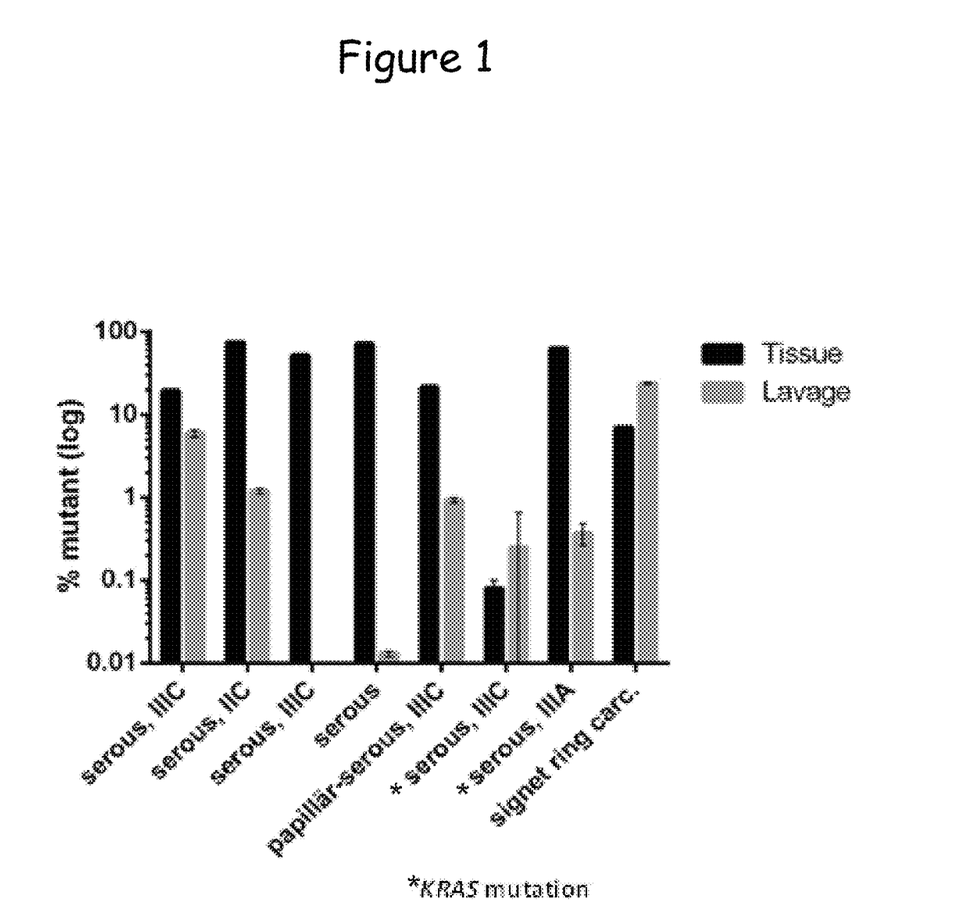
FIG. 1 shows the TP53, KRAS mutational analysis of matched tumor tissue and lavage samples.

6. Determine a Biomarker Indicative of OC and/or EC, or a Precursor Malignancy thereof, in 7 Patient Samples DNA of the lavage of 7 patients has been analyzed for the presence of specific genetic changes of the respective tumor tissue. This was in 4 patients a TP53 point mutation, in 1 patient a TP53 deletion of one codon, in 1 patient a TP53 and additionally a KRAS mutation, and in 1 patient a KRAS mutation, which means that overall it was tested for 8 genetic changes. 6 patients had epithelial ovarian cancer (EOC), one a signet ring carcinoma, metastasized in the ovaries. The results in Table 1 and FIG. 1 show mean and standard deviation of two to three testings.

Seven out of eight tested genetic changes could be detected in the corresponding lavage specimens, with a rate between 0.013% and 5.96% in the EOC and 23.8% in the signet ring carcinoma patient. Only in one case the specific TP53 mutation could not be detected. This can be explained by the fact, that especially in advanced stage tumor patients, the function of the fallopian tubes is not given anymore.

Figure 2:
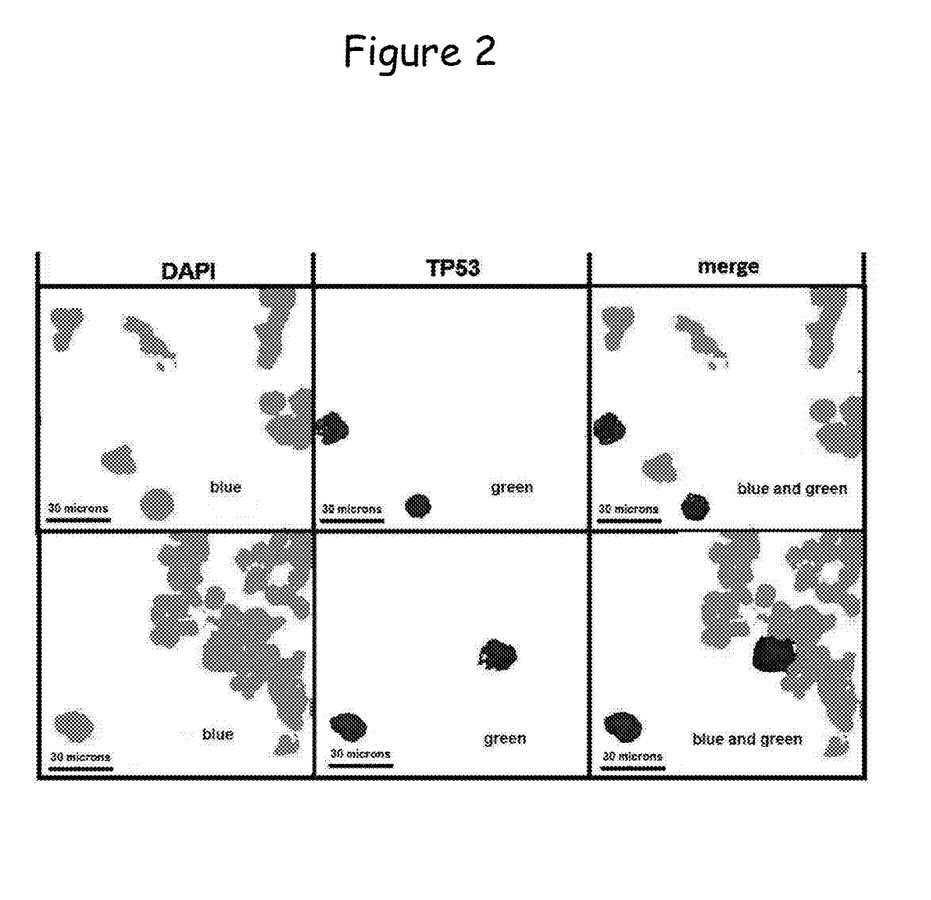
FIG. 2 shows TP53 immunofluorescence staining of uterine lavage sample. The first column shows DAPI fluorescent staining (originally imaged in blue), the second column shows TP53 (originally imaged in green), and the third column shows the combined image of each row.

The presence of cancer cells in the lavage fluid was further confirmed through p53 immunofluorescence staining (see FIG. 2), applying a filter method.

This preliminary results proof that tumor cells can indeed be collected by this lavage technique in patients with HGSC or other malignant abdominal diseases.

TABLE 1

TP53, KRAS mutational analysis of matched tumor tissue and lavage samples

| Pat. No. | Diagnosis | Genetic change | tissue mean | tissue SD | lavage mean | lavage SD |
|---|---|---|---|---|---|---|
| 1 | serous, IIIC | p53_282 | 19.35% | 0.71% | 5.96% | 0.63% |
| 2 | serous, IIC | p53_248 | 74.28% | 1.24% | 1.20% | 0.09% |
| 3 | serous, IIIC | p53_135 | 52.30% | 1.13% | 0% | 0 |
| 4 | serous | p53_245 | 72.15% | 0.21% | 0.013% | 0.001% |
| 5 | papillary-serous, IIIC | p53_del170 | 21.55% | 0.21% | 0.93% | 0.06% |
| 1 | serous, IIIC | KRAS_G12D | 0.08% | 0.02% | 0.25% | 0.41% |
| 6 | serous, IIIA | KRAS_G12D | 62.48% | 0.00% | 0.37% | 0.11% |
| 7 | signet ring carcinoma | p53_282 | 6.98% | 0.35% | 23.80% | 0.21% |

The invention claimed is:

1. A method for treating ovarian cancer (OC) and/or endometrial cancer (EC) in a human subject, comprising:
   (a) flowing a liquid into a human subject's uterine cavity and fallopian tubes;
   (b) aspirating a liquid sample from the uterine cavity and fallopian tubes, wherein said flowing and said aspirating occur simultaneously;
   (c) fractionating said liquid sample to obtain a cell fraction of epithelial cells;
   (d) identifying at least one nucleotide or amino acid mutation in TP53 associated with OC or EC in said cell fraction of epithelial cells using a method selected from the group consisting of a protein binding assay, a nucleic acid hybridization assay, a nucleic acid amplification assay, and nucleotide sequencing, wherein the presence of at least one mutation in TP53 associated with OC or EC identifies OC or EC in the human subject; and
   (e) treating the human subject for OC or EC prior to the onset of symptoms of OC or EC in the human subject, wherein the treatment is selected from the group consisting of surgery and chemotherapy.

2. The method of claim 1, wherein the liquid is normal saline solution (NISR).

3. The method of claim 1, wherein nucleic acid is extracted from the epithelial cells.

4. The method of claim 1, wherein a nucleic acid sequence is determined.

5. The method of claim 1, wherein the OC or EC is an intraepithelial carcinoma of the fallopian tubes or of the endometrial lining.

6. The method of claim 1, wherein immunocytochemistry or fluorescence in situ hybridization (FISH) is employed.

7. The method of claim 1, wherein the epithelial cells are serous tubal intraepithelial carcinoma cells or serous endometrial intraepithelial carcinoma cells.

8. The method of claim 1, wherein the protein binding assay is selected from the group consisting of an ELISA assay, flow cytometric analysis, a radioimmunoassay, and a Western blot assay.

9. The method of claim 1, wherein the OC or EC identified in the human subject is stage II OC or stage II EC.

* * * * *